(12) United States Patent
Frei et al.

(10) Patent No.: US 6,974,247 B2
(45) Date of Patent: Dec. 13, 2005

(54) DEVICE FOR MIXING AND/OR INJECTING CEMENTS

(75) Inventors: Christian Frei, Basel (DE); Beat Ehrsam, Oberdorf (DE)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/963,279

(22) Filed: Oct. 11, 2004

(65) Prior Publication Data

US 2005/0111299 A1   May 26, 2005

Related U.S. Application Data

(63) Continuation of application No. PCT/CH02/00204, filed on Apr. 11, 2002.

(51) Int. Cl.$^7$ ............................................... B01F 13/00
(52) U.S. Cl. ..................................... 366/255; 366/332
(58) Field of Search ............................... 366/130, 139, 366/189, 255–260, 285–286, 332–335; 206/219

(56) References Cited

U.S. PATENT DOCUMENTS

| | | | |
|---|---|---|---|
| 3,140,078 A * | 7/1964 | Grubb et al. ............... | 366/256 |
| 3,417,971 A | 12/1968 | Blank et al. | |
| 4,010,934 A | 3/1977 | McCord et al. | |
| 4,208,133 A * | 6/1980 | Korte-Jungermann ....... | 366/130 |
| 4,469,153 A * | 9/1984 | Morrisette .................. | 366/256 |
| 4,676,406 A * | 6/1987 | Frischmann et al. ........ | 222/136 |
| 4,676,655 A * | 6/1987 | Handler ...................... | 366/130 |
| 4,758,096 A | 7/1988 | Gunnarsson | |
| 4,799,801 A * | 1/1989 | Bruning ...................... | 206/219 |
| 5,284,389 A * | 2/1994 | Lumsden ..................... | 366/332 |
| RE35,276 E * | 6/1996 | Chan ............................ | 206/219 |
| 2005/0111299 A1 * | 5/2005 | Frei et al. ................... | 366/255 |

FOREIGN PATENT DOCUMENTS

| | | |
|---|---|---|
| DE | 297 21 534 U | 3/1998 |
| EP | 0330723 A2 * | 9/1989 |
| EP | 0 987 055 A | 3/2000 |
| FR | 2 119 650 | 8/1972 |
| WO | 99/67015 A1 * | 12/1999 |

* cited by examiner

Primary Examiner—Charles E. Cooley
(74) Attorney, Agent, or Firm—Jones Day

(57) ABSTRACT

The present invention relates to a device for storing and/or mixing and/or injecting cements, especially bone cements. The device includes a tube having a longitudinal axis, a front end with an outlet opening, a rear end; and an internal cylindrical cavity having a first end and a second end; a locking mechanism detachably connected to the front end of the tube so that the outlet opening can be sealed; and a lid detachably connected to the rear end of the tube; the lid having a borehole extending therethrough. The device also includes: a mixer having a mixing shaft sized and configured to extend through the borehole formed in the lid and a mixing tool at one end thereof, the mixer being axially and rotationally moveable inside of the cavity; a driving mechanism connected to the mixer shaft so that the mixer can be axially and rotationally moved with respect to the tube; and a first restraining mechanism for limiting the axial movement of the mixer with respect to the tube so that the a minimum distance A remains between the front face of the mixing tool and the front wall of the cavity; wherein the cylindrical cavity has a diameter D and the mixing tool has a maximum dimension X such that X is less than D.

14 Claims, 2 Drawing Sheets

DEVICE FOR MIXING AND/OR INJECTING CEMENTS

Continuation of prior application No.: PCT/CH02/00204 filed Apr. 11, 2002.

BACKGROUND OF THE INVENTION

The present invention relates to a device for storing and/or mixing and/or injecting cements, especially bone cements.

Many of the present-day cements, which are produced from two components, a powdery component and a liquid component, polymerize after the components are mixed thoroughly and subsequently form a hard and more or less permanent cement composition. Aside from the polymerizable cements, so-called hydraulic cements, such as phosphate cements, may also be used.

Polymethacrylates, which are also referred to as PMMA, are most frequently used as bone cements at the present time. PMMA include a powdery polymer and a liquid monomer. When mixed, these components polymerize within minutes and form a firm connection between the prosthesis and the bone structure surrounding the prosthesis.

In addition, calcium phosphate cements are also increasingly used at the present time. Here also, a powdery component is mixed with a liquid component. After the components are mixed, the cement is hardened by a precipitation reaction.

Devices for mixing and metering pharmaceutical products are known. For example, German Patent No. DE 297 21 534 discloses a mixing and metering container which comprises a container body, which includes an internal cylindrical space having an outlet with a tapering diameter at one end and a piston unit at the other end of the container body. The piston unit seals the end of the container body and is axially movable in the internal cylindrical space. The piston unit has an opening for receiving a drive shaft of a mixing tool, which can be driven into the internal cylindrical space. The container also includes a driving device, which engages the opening and is connected to the container body. However, the driving device can only be connected to the container body after the mixing tool is removed. The piston unit is moved by a threaded rod, the threaded rod being actuated manually by an actuating element at the end of the driving device. It is a disadvantage of this known device that an adequate distance between the mixing tool and the wall of the mixing space is not necessarily ensured so that, when abrasive powders are mixed, there may be appreciable wear on the mixing tool and/or on the wall of the mixing space, the abraded particles having a negative effect on the quality of the product.

SUMMARY OF THE INVENTION

The present invention attempts to provide a remedy for the disadvantages associated with the prior art. That is, it is an object of the invention to provide a device for mixing a two-component cement, the device including restraining means for the mixing tool so that a minimum distance is maintained between the mixing tool and the wall of the mixing space thereby reducing abrasion on the mixing tool and/or on the wall of the mixing space.

The present invention may be used with different cements. In particular, the present invention is suitable for the preparation of so-called bone cements, which may be used for anchoring and supporting artificial joint components and other prostheses.

Pursuant to the invention, this objective is accomplished with a device for storing, mixing, and/or injecting cements, especially bone cements, wherein the device includes a tube having a longitudinal axis, a front end with an outlet opening, a rear end; and an internal cylindrical cavity, i.e., the mixing space, having a first end and a second end; a locking mechanism detachably connected to the front end of the tube so that the outlet opening can be sealed; a lid detachably connected to the rear end of the tube; the lid having a borehole extending therethrough; a mixer comprising a mixing shaft sized and configured to extend through the borehole formed in the lid and a mixing tool at the other end thereof, the mixer being axially and rotationally moveable inside of the cylindrical cavity; driving means connected to the mixer shaft so that the mixer can be axially and rotationally moved with respect to the tube; and first restraining means for limiting the axial movement of the mixer with respect to the tube so that the a minimum distance A remains between the front face of the mixing tool and the first end of the cavity; wherein the cylindrical cavity has a diameter D and the mixing tool has a maximum dimension X such that X is less than D.

The present device may also include a tube with an outlet opening at a front end thereof and a lid which can be detachably connected at a rear end thereof. The lid being detachably connected to the tube by a first locking means. The lid having a borehole, which is coaxial with the longitudinal axis of the tube. The device also includes a mixer with a mixing tool, which can be moved axially and rotationally in a cavity formed in the tube, and a mixing shaft, which passes through the borehole formed in the lid. The mixing shaft can be connected outside of the tube to a driving means in order to facilitate the axial and rotational movement of the mixer. A locking mechanism may be detachably connected to the front end of the tube. The locking mechanism includes an axially continuous, central borehole, which is connected to the outlet opening of the tube so that the central borehole and hence the outlet opening can be closed off by a membrane. Thus, on the one hand, the outlet opening may be closed off by the membrane and, on the other hand, the liquid component of the cement can be injected through the membrane without opening the device. Furthermore, the device may include restraining means, by means of which the displacement of the mixing tool parallel to the longitudinal axis can be limited at least at the front end of the tube.

In the preferred embodiment of the inventive device, the device includes a piston, which can be introduced into the cavity formed in the tube from the rear end of the tube. The piston being axially moveable within the cavity. The piston including a sealing lip concentric with the longitudinal axis so that the front portion of the cavity, i.e., the portion in front of the piston, is sealed off from the rear portion of the cavity, i.e., the portion behind the piston. The piston also includes a through hole extending therethrough coaxially with the longitudinal axis so that the shaft of the mixer can be mounted through the through hole formed in the piston. Furthermore, the rear end of the tube can be closed off by a detachable a lid which includes a borehole, coaxial with the longitudinal axis of the cavity, so that the mixing shaft can also be passed through the borehole formed in the lid. The device may also include restraining means configured so that the driving means, when the mixing tool is in its position closets to the front end of the tube, comes to rest on what is regarded, with respect to the cavity, as the outside of the lid, so that a minimum distance A remains between the mixing tool and the front cavity wall thereby forming an axial boundary between the front face of the mixing tool and the first end of the cavity. This minimum distance A preferably is between twice and five times the diameter of the particles of the material being mixed. For example, for bone cements, the diameter of the particles may fall within the following ranges:

between 5 $\mu$m and 50 $\mu$m
between 50 $\mu$m and 800 $\mu$m or
between 5 $\mu$m and 800 $\mu$m.

Thus, the minimum distance A between the front face of the mixing tool and the front cavity wall may be:

10 $\mu$m and 250 $\mu$m, or between
100 $\mu$m and 4000 $\mu$m, or between
10 $\mu$m and 4000 $\mu$m.

Preferably, the cavity is coaxial with the longitudinal axis of the tube and is cylindrically configured with a diameter D, when measured perpendicular to the longitudinal axis. Preferably, the diameter D is larger than the maximum dimension X of the mixing tool, when measured perpendicular to the longitudinal axis, the difference between the diameter D and the maximum dimension X ($\Delta=D-X$) preferably being between 4 times and 10 times the diameter of the largest particle of the material being mixed. Thus, in the various embodiments of the inventive device, this difference $\Delta$ may be between:

20 $\mu$m and 500 $\mu$m, or between
200 $\mu$m and 8000 $\mu$m, or between
20 $\mu$m and 8000 $\mu$m.

The diameter of the mixing shaft and the diameter of the through hole formed in the piston are such, that the mixing shaft has a slight clearance in the through hole so that movement of the mixer does not move the piston during the mixing process.

In a different embodiment of the inventive device, the device may include second restraining means, which are configured so that the axial displacement of the mixing tool is also limited towards the rear end of the tube so that the mixing tool, when it is in its position closest to the rear end of the tube, is at a minimum distance B from the front face surface of the piston, which is also pushed into its position closest to the rear end of the tube. Preferably, the minimum distance B corresponds to the minimum distance A.

Because of (1) the distance A of the mixing tool from the front cavity wall, (2) the difference $\Delta$ of the mixing tool from the lateral cavity wall, and (3) the distance B of the mixing tool for the front face surface of the piston, the present device ensures that there is no or only very little wear on the cavity wall, the mixing tool and/or on the piston during mixing of the abrasive particles. As previously stated, these distances should advantageously be more than twice the diameter of the particles.

In a further embodiment of the inventive device, the first restraining means includes a first axial stop, mounted on the driving means. The first axial stop preferably being constructed so that the driving means is sized and configured to contact the lid, when the mixing tool is in its position closest to the first end of the cavity.

In yet another embodiment of the inventive device, the second restraining means includes a second axial stop, mounted on the mixing shaft and on the lid. The second axial stop preferably is constructed so that the cross-sectional surface of the mixer shaft, orthogonal to the longitudinal axis, is reduced in size at a distance $L_1$ from the front end of the mixing tool and, complementary thereto, at a distance $L_2$ from the inner surface of the lid, the cross-sectional surface of the borehole formed in the lid, which is also orthogonal to the longitudinal axis, is reduced in size. The distances $L_1$ and $L_2$ depend on the axial thickness of the mixing tool, the minimum distance B and the length of the piston.

Furthermore, the first locking means, which detachably connects the lid to the rear end of the tube, can be configured in various different embodiments, such as a bayonet-type connection, a screw connection, a snap fit connection, etc.

Analogously to the first locking means, the second locking means, which detachably connects the locking mechanism to the front end of the tube, can also be configured in various different embodiments, such as a bayonet-type connection, a screw connection, a snap fit connection, etc.

Moreover, the driving means for the axial and/or rotational movement of the mixer consists preferably of a handle. However, in other embodiments of the inventive device, the driving means can be constructed as an electrically, pneumatically or hydraulically working driving machine.

The present invention provides a device wherein none of the material originating from the mixing container or the mixing tool reaches the material being mixed because of the distance between the mixing tool and the mixing container. This is extremely important for implant materials, since particles of certain materials can lead to undesirable effects in the body. Moreover, the powdery components of the cement can be stored in the inventive device and mixed with the liquid component at the desired time. Subsequently, the mixture can be injected directly from the mixing space to the desired location. Thus, the present device ensures that the material to be mixed is protected at all times from the environment and from possible contaminations therewith.

BRIEF DESCRIPTION OF THE DRAWINGS

The invention and further developments of the invention are described in even greater detail in the following by means of the partially diagrammatic representations of several examples. In the drawing

DESCRIPTION OF THE PREFERRED EMBODIMENTS

Figure 1:
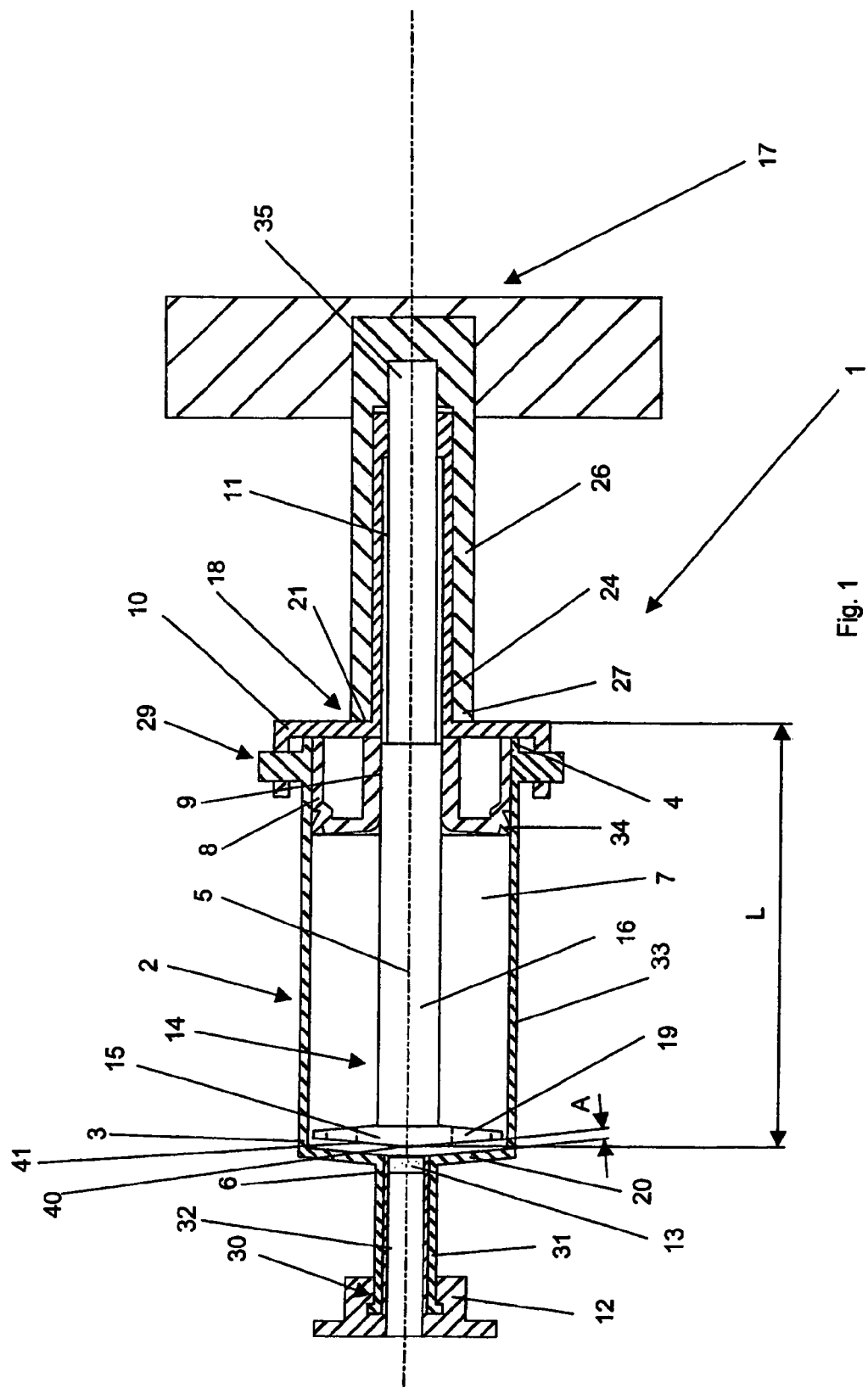
FIG. 1 shows a longitudinal section through an embodiment of the inventive device, the mixer being in its position closest to the front end of the tube

FIG. 1 shows an embodiment of the inventive device 1 with a tube 2 and a mixer 14, which is shown in its position closest to the front end 3 of the tube 2. The tube 2 is configured with a hollow, cylindrical cavity 7 which is concentric with the longitudinal axis 5. The cavity 7 having a cross sectional area Q extending orthogonal to the longitudinal axis 5. The mixer 14 is axially moveable along the longitudinal axis 5 of the tube 2 and can be rotated about the longitudinal axis 5. The tube 2 includes a front cavity wall 20, which extends generally transverse to the longitudinal axis 5, and a lateral wall 33, which extends generally parallel to the longitudinal axis 5. The front end 3 of the tube 2 has an outlet opening 6 with a cross-sectional area q extending orthogonal to the longitudinal axis 5. The cross-sectional area q of the outlet opening is smaller than the cross-sectional area Q of the cavity 7.

The rear end 4 of the tube 2 includes a first locking means 29, which is disposed on the external wall of the tube 2. The first locking means 29 fastens a detachable lid 10 to the rear end 4 of the tube 2. In the preferred embodiment of the inventive device 1 shown here, the first locking means 29 is configured as bayonet-type connection. Similarly, the front end 3 of the tube 2 may include a tubular attachment 31, which is disposed coaxially with the longitudinal axis 5 and aligned with the outlet opening 6. Second locking means 30 are disposed on the tubular attachment 31 so that a locking mechanism 12 can be detachably fastened to the tubular attachment 31 so that the cavity 7 can be closed off, i.e., sealed, at the front end 3 of the tube 2. The locking mechanism 12 may be pushed into the tubular attachment 31, coaxially along the longitudinal axis 5, and up to the outlet opening 6. The locking mechanism 12 has a central borehole 32, which is coaxial with the longitudinal axis 5 and which can be closed off by means of a membrane 13.

The device 1 may also include a piston 8, which is also axially moveable in the cavity 7 of the tube 2 along the longitudinal axis 5. As shown in FIG. 1, the piston 8 is in its rear position at the rear end 4 of the tube 2. The piston 8 serves to meter, ie., discharge, the mixed material, which, as the piston 8 moves parallel to the longitudinal axis 5 towards the front end 3 of the tube 2, emerges from the outlet opening 6. The piston 8 also includes a through hole 9, which is coaxial with the longitudinal axis 5 and which accommodates and guides the shaft 16 of the mixer 14, i.e., the mixer shaft. The piston 8 may also include a sealing lip 34, which is disposed concentrically with the longitudinal axis 5 and by means of which the cavity 7 can be sealed off from the rear end 4 of the tube 2.

As shown in FIG. 1, the lid 10 is detachably mounted at the rear end 4 of the tube 2 and includes a borehole 11, which extends coaxially along the longitudinal axis 5 through the lid 10. The lid 10 may also further include a tube 24, which is coaxial with the longitudinal axis 5, and through which the borehole 11 coaxially passes so that the mixer shaft 16 can be axially passed through the lid 10 and through the tube 24.

The mixer 14 may also include driving means 17 disposed at the rear end 35 of the mixer shaft 16 axially opposite to the mixing tool 15. As shown, the driving means 17 may be constructed as a handle. As previously stated, the mixer 14 is axially and rotationally moveable inside of the cavity 7 and comprises a mixing tool 15 and a mixer shaft 16, which can be passed through the through hole 9 formed in the piston 8 and the borehole 11 formed in the lid 10 and in the tube 24. The mixing tool 15 is equipped with ports 19, which extend completely through the mixing tool 15 parallel to the longitudinal axis 5.

The device 1 may also include first restraining means 18, which limit the axial displacement of the mixer 14 in the direction of the front end 3 of the tube 2 in such a manner that, when the mixing tool 15 is in its position closest to the front end 3 of the tube 2, a minimum distance A remains between the front face wall 41 of the mixing tool 15 and the front wall 20 of the cavity 7. In this embodiment of the inventive device 1, the first restraining means 18 consists of a first axial stop 21 wherein the front end 27 of the tubular continuation 26 of the driving means 17 contacts the exterior surface of the lid 10 so that the minimum distance A between the front face wall 41 of the mixing tool 15 and the front wall 20 of the cavity 7 is maintained. That is, the mixer shaft 16 is connected to the driving means 17 in such a manner that a length L is maintained between the front end 40 of the mixing tool 15, which is directed towards the outlet opening 6, and the front end 27 of the tubular continuation 26 of the driving means 17. The length L being determined by the length of the cavity 7 in the tube 2, the thickness of the lid 10 and the minimum distance A.

Figure 2:
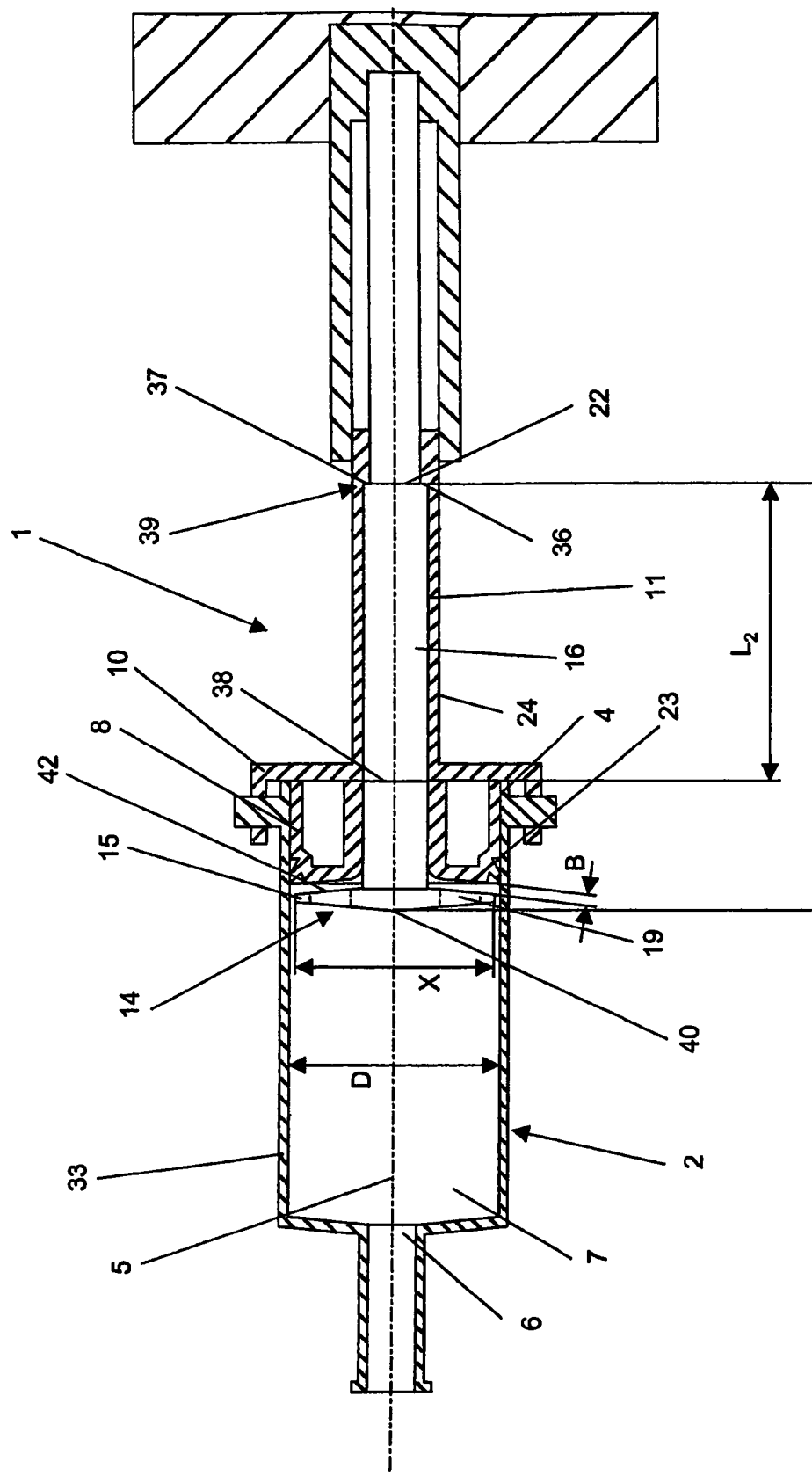
FIG. 2 shows a longitudinal section through the embodiment of the inventive device, shown in FIG. 1, the mixer being in its position closest to the rear end of the tube.

In FIG. 2, the mixing tool 15 and the piston 8 are in their position closest to the rear end 4 of the tube 2. The device 1 preferably includes a second restraining means 39, which limits the axial displacement of the mixer 14 with respect to the rear end 4 of the tube 2. The second restraining means 39 includes a second axial stop 22, which, as shown, is configured as a first cross-sectional reduction in size 36 of the cross-sectional surface of the mixer shaft 16 and a complementary second cross-sectional reduction in size 37 of the cross-sectional surface of the borehole 11. Through the inter-engagement of the second restraining means 39, it can be achieved that, when the mixing tool 15 is in its position closest to the rear end 4 of the tube 2, a minimum distance B remains between the rear face wall 42 of the mixing tool 15 and the front face surface 23 of the piston 8. For this purpose, the length $L_1$ between the front end 40 of the mixing tool 15 and the first cross-sectional reduction in size 36 formed on the mixer shaft 16 and the length $L_2$ between the inside surface of the lid 10, directed towards the cavity 7, and the second cross-sectional reduction in size 37 formed in the borehole 11 are dimensioned so that the difference in lengths ($L_1$–$L_2$) corresponds to the sum of the axial dimensions of the mixing tool 15, the length of the piston 8 and the minimum distance B.

Furthermore, as seen perpendicularly to the longitudinal axis 5, the maximum dimension X of the mixing tool 15 is smaller than the diameter D of the cavity 7 formed in the tube 2, orthogonal to the longitudinal axis 5, so that the mixing tool 15 is at a distance from the side wall 33 of the cavity.

At the end of the mixing process, after the lid 10 is loosened and retracted, the mixer shaft 16 can be broken off at a predetermined breaking point 38 so that the metering, i.e., discharging, of the cement by means of the piston 8 and a driving device (not shown) suitable for this purpose is not impeded by the mixer shaft 16, the lid 10 or the driving means 17. A manually operated rocker, such as that disclosed in European Patent No. 0 326 551, for example, may be used as a driving device. In use, the mixed cement is metered and discharged through the outlet opening 6 by the piston 8 in the cavity 7. At the same time, the mixing tool 15 is in a retracted position adjoining the front face surface 23 of the piston 8 and is also moved by the piston 8.

What is claimed is:

1. A device for storing, mixing, and/or injecting cements, the device comprising:

a tube having a longitudinal axis, a front end with an outlet opening, a rear end; and an internal cylindrical cavity including a first end with a front wall and a second end;

a locking mechanism detachably connected to the front end of the tube so that the outlet opening can be sealed;

a lid detachably connected to the rear end of the tube; the lid having a borehole extending therethrough;

a mixer having a mixing shaft sized and configured to extend through the borehole formed in the lid and a mixing tool at an end thereof, the mixing tool having a front face surface, the mixer being axially and rotationally moveable inside of the cavity;

driving means connected to the mixer shaft so that the mixer can be axially and rotationally moved with respect to the tube; and first restraining means for limiting the axial movement of the mixer with respect to the tube so that a minimum distance A remains between the front face surface of the mixing tool and the front wall of the cavity;

wherein the first restraining means comprises a first axial stop which is mounted on the driving means and which limits the axial displacement of the mixer with respect to the tube in the direction of the front end of the tube;
wherein the cylindrical cavity has a diameter D and the mixing tool has a maximum dimension X such that X is less than D.

2. The device of claim 1, wherein the distance A is between 10 µm and 4000 µm.

3. The device of claim 2, wherein the distance A is between 25 µm and 1600 µm.

4. The device of claim 1, wherein the device further includes a piston having a front face surface which is axially displaceable in the cavity, parallel to the longitudinal axis, the front face surface having a through hole extending therethrough so that the mixer shaft can be passed through the through hole formed in the piston and through the borehole formed in the lid; the device further including second restraining means comprising an axial stop formed between the mixer shaft and the borehole so that the axial movement of the mixer is limited when the mixer is moved in the direction of the rear end of the tube so that, when the piston and the mixing tool are in their position closest to the second end of the cavity, there is a minimum distance B between the mixing tool and the front face surface of the piston.

5. The device of claim 4, wherein the distance B is between 10 µm and 4000 µm.

6. The device of claim 5, wherein the distance B is between 25 µm and 1600 µm.

7. The device of claim 4, wherein the lid includes, parallel to the longitudinal axis, a tube which extends towards the driving means, the tube having a borehole extending therethrough, and the axial stop of the second restraining means is formed by a reduction in size of the cross-sectional surface of the mixer shaft and a complementary reduction in size of the cross-sectional surface of the borehole.

8. The device of claim 4, wherein the piston further includes a sealing lip, which is concentric with the longitudinal axis.

9. The device of claim 1, wherein the driving means has a tubular continuation with a front end directed against the lid, the front end of the tubular continuation being at a distance L, measured parallel to the longitudinal axis, from the front face surface of the mixing tool, the length L being dimensioned so that the front end of the tubular continuation contacts the lid when the mixing tool is in its position closest to the first end of the cavity.

10. The device of claim 1, wherein the difference between the diameter D and the dimension X is between 20 µm and 8000 µm.

11. The device of claim 10, wherein the difference between the diameter D and the dimension X, is between 50 µm and 3200 µm.

12. The device of claim 1, wherein the lid is detachably connected to the tube by means of a bayonet-type connection.

13. The device of claim 12, wherein the piston is moved by means of a driving device, which is detachably connected to the tube by means of the bayonet type connection.

14. The device of claim 1, wherein the front end of the tube further includes a tubular attachment, which is disposed coaxially with the outlet opening and the tubular attachment comprises a membrane for sealing off the outlet opening.

* * * * *